(12) United States Patent
Daugan

(10) Patent No.: US 6,608,065 B1
(45) Date of Patent: Aug. 19, 2003

(54) USE OF CGMP PHOSPHODIESTERASE INHIBITORS IN METHODS TO TREAT FEMALE SEXUAL DYSFUNCTION

(75) Inventor: Alain Claude-Marie Daugan, Les Ulis (FR)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 09/573,905

(22) Filed: May 18, 2000

Related U.S. Application Data

(63) Continuation of application No. 08/981,989, filed as application No. PCT/EP96/03024 on Jul. 11, 1996, now Pat. No. 6,140,329.

(30) Foreign Application Priority Data

Jul. 14, 1995 (GB) .............................. 9514464

(51) Int. Cl.[7] ...................... A61K 31/50; A61K 31/495; A61K 31/40
(52) U.S. Cl. ...................... 514/250; 514/249; 514/292; 514/408; 514/410
(58) Field of Search ................................ 514/250, 249, 514/292, 410, 408

(56) References Cited

U.S. PATENT DOCUMENTS

| | | | |
|---|---|---|---|
| 3,644,384 A | 2/1972 | Schulenberg | ............ 260/295 C |
| 3,717,638 A | 2/1973 | Schulenberg | ......... 260/268 PC |
| 3,917,599 A | 11/1975 | Saxena et al. | ........ 260/268 PC |
| 4,188,390 A | 2/1980 | Campbell | .................... 424/251 |
| 4,686,228 A | 8/1987 | Campbell et al. | ............ 514/307 |
| 5,145,852 A | 9/1992 | Virag | ......................... 514/253 |
| 5,270,323 A | 12/1993 | Milne, Jr. et al. | ........... 514/309 |

FOREIGN PATENT DOCUMENTS

| | | | |
|---|---|---|---|
| EP | 0 357 122 | 3/1990 | ......... C07D/471/04 |
| EP | 0 362 555 | 4/1990 | ......... C07D/241/08 |
| EP | 459 666 | 12/1991 | ......... A61K/31/505 |
| EP | 463 756 | 1/1992 | ......... C07D/487/04 |
| EP | 526004 | 2/1993 | ......... C07D/487/04 |
| GB | 1 454 171 | 10/1976 | ......... C07D/471/14 |
| JP | 03044324 A | 2/1991 | .......... A61K/31/52 |
| WO | WO 89/10123 | 11/1989 | .......... A61K/31/35 |
| WO | WO 94/28902 | 12/1994 | ......... A61K/31/505 |
| WO | WO 95/19978 | 7/1995 | ......... C07D/471/14 |

OTHER PUBLICATIONS

Read, J., International Review of Psychiatry, (1995), 7/2, 175–182.*
Hurlbert, et al., J. Sex and Marital Therapy, 1993 19/2 154–165.*
Stedman's Medical Dictionary, William & Wilkins, 1995, one page.*
Beyer et al., Phys. and Behav., (1981), 27, 731–733.
Pickard et al., Br. J. Pharmacol., (1991), 104 755–759.
Martinez–Pineiro et al., Eur. Urol., (1993), 24, 492–499.
Mirone et al., Br. J. Urol., (Mar., 1993), 71(3), 365.
Murray et al., Biochemical Soc. Trans., (1992), 20, 460–464.
Raeburn et al., Prog. Drug Res., (1993), 12–32.
Merkel, Cardio. Drug. Rev., (1993), 11(4), 501–515.
"Physicians' Desk Reference," (1992) 2207–2208.
Cimino et al., Biochem. Pharmacology, (1988), 37(14), 2739–2745.
Watanabe et al., Federation Proceedings, (1982), 41(7), 2292–2399.
Earl et al., Life Sciences, (1984), 35, 525–534.
Brindley, Brit. J. Phychiat., (1983), 19, 108–112.
Funderbunk, New Engl. J. Med., (1974), 290, 630–631.
Beretta, Acta European Fertilitatis, (1986), 17, 43–45.
"Physicians' Desk Reference," (1992), 1778–1779.
Hess in "Prazosin: Evaluation of a New Antihypertensive Agent," D. Cotton ed., American Elsevier, NY, (1974), 3–15.
Dadkar et al., Ind. J. Exp. Biol., (1982), 20, 484–487.
D'Armiento et al., Eur. J. Pharmacol., (1980), 65, 234–247.
Bhalla et al., Brit. Med. J., (1979), 2, 1059.
Burke et al., Med. J. Aust., (1980), 382–383.
Segasouthy et al., Med. J. Malaysia, (1982), 37(4), 384.
Ylitalo et al., Acta Med. Scand., (1983), 213, 319–320.
Robbins et al., J. Urol., (1983), 130, 975.
Adams et al., J. Urol., (1984), 132, 1208.
Russell et al., Med. J. Aust., (1985), 143, 321.
Taher et al., Int. J. Impotence Res., Abstracts, Milan, Italy (Sep. 14–17, 1992).
Trigo–Rocha et al., Neurourology and Urodynamics, 13, (1994), 71–80.
Saxena et al., Journal of Medicinal Chemistry, vol. 16, No. 5, 560–564 (1973).
Ishida et al., Chem. Pharm. Bull., vol. 33, No. 8, 3237–3249 (1985).
Gillespie et al., Molecular Pharmacology, 36:773–781 (1989).
Braña et al., Synthetic Communications, 20(12), 1793–1820 (1990).
Dellouve–Courillon et al., Tetrahedron, 46, No. 9, 3245–3266 (1990).
Murray, DN&P 6(3), 150–156 (1993).
Zorgniotti et al. Int. J. Impotence Res., 6, 33–36 (1994).
A. Bowman et al., Br. J. Pharmac., (1984), 81, 665–674.
F. Trigo–Rocha et al., Am. J. Physiol., (Feb., 1993), 264, H419–H422.
J. Reiser et al., Br. J. Dis. Chest, (1986), 80, 157–163.
P. Bush et al., J. Urol., (Jun., 1992), 147, 1650–1655.
F. Holmquist et al., J. Urol. (Oct., 1993), 150, 1310–1315.

(List continued on next page.)

Primary Examiner—Sreeni Padmanabhan
Assistant Examiner—S. Jiang
(74) Attorney, Agent, or Firm—Marshall, Gerstein & Borun

(57) ABSTRACT

The use of (6R, 12aR)-2,3,6,7,12,12a-hexahydro-2-methyl-6-(3,4-methylenedioxyphenyl)-pyrazino[2',1':6,1]pyrido[3,4-b]indole -1,4-dione, (3S, 6R, 12aR)-2,3,6,7,12,12a-hexahydro-2,3-dimethyl-6-(3,4-methylenedioxyphenyl) pyrazino[2', 1':6,1]pyrido[3,4-b]indole-1,4-dione, and physiologically acceptable salts and solvates thereof, in the treatment of impotence.

8 Claims, No Drawings

OTHER PUBLICATIONS

R. Rudd et al., *Br. J. Dis. Chest*, (1983), 77, 78–86.
E. McMahon et al., *J. Pharmacol. Exp. Thera.*, (1989), 251, 1000–1005.
F. Holmquist et al., *Acta Physiol. Scand.*, (1991), 143, 299–304.
G. Barbanti, *Urol. Res.*, (1988), 16, 299–302.
L. Ignarro et al., *Biochem. and Biophys. Res. Comm.*, (1990), 170(2), 843–850.
J. Krall et al., *Bio. Reprod.*, (1988), 39, 913–922.
M. Wilkins et al., *Proc. Natl. Acad. Sci., USA*, (Aug., 1990), 87, 6465–6469.
M. Wilkins et al., *J. Clin. Invest.*, (Apr., 1990), 85, 1274–1279.
J. Rajfer, *N. Eng. J. Med.*, (Jan., 1992), 326(2), 90–94.
H. Knispel, *Urol. Res.*, (1992), 20, 253–257.
G. Gwinup, *Annals. of Internal Medicine*, (Jul., 1988), 162–163.
A. Zorgniotti, *J. Urol.*, (Apr., 1992), 147(4), 308A.
K. Azadzoi et al., *J. Urol.*, (Nov., 1992), 148, 1587–1591.
K. Azadzoi et al., *J. Urol.*, (Jan., 1992), 147, 220–225.
C. Sparwasser et al., *J. Urol.*, (Dec., 1994), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs," Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharmacol.*, (1986), 35:10, 1743–1751.
J. Doremieux et al., *Ann. Urol. Paris*, (1987), 21(6), 429–434.
D. Green et al., *Geriatrics*, (Jan., 1993), 48(1), 46–58.
M. Webster et al., *Hematol. Oncol. Cl. of N. Am.*, (Feb., 1990), 4(1), 265–289.
F. Holmquist et al., *Acta. Physiol. Scand.*, (1991), 141, 441–442.
J. Taher et al., *J. Urol.*, (Apr., 1993), 149, 285A.
S. Uckert et al., *J. Urol*, (5 Supp.), 495A, (1994).
W. Aronson et al., *J. Urol.*, (1991), 145 (4 Supp.), 341A.
P. Bush et al., *Fed. Am. Soc. Exp. Biol.*, (1991), 5(4), 175.
P. Bush et al., *Fed. Am. Soc. Exp. Biol.*, (1992), 6(4), 2092.
W. Aronson et al., *J. Urol.*, (1992), 147 (4 Supp.), 454A.
P. Bush et al., *Circulation*, (May, 1993), 87 Supp. V, V–30–V–32.
R. Pickard et al., *J. Urol.*, (May, 1993) 149 (4 Supp.), 245A.
R. Pickard et al., *Clin. Pharmacol.*, (Jan., 1993), 35(5), 536P–537P.
F. Trigo–Rocha et al., *J. Urol.*, (Apr., 1993), 149, 872–877.
M. Krupp et al., *J. Cardiovas. Pharmacol.*, (1989), 13 (Supp. 2), S11–S19.
"Physicians' Desk Reference," (1992), 683, 1099–1100, 1344, 1941–1943.
R. Morales et al., *World J. Urol.*, (1990), 8, 80–83.
J. Cortijo, *Br. J. Pharmacol.*, (Feb., 1993), 108(2), 562–568.
E. Kim et al., *J. Urol.*, (1995), 153, 361–365.
S. Korenman et al., *JAGS*, (Apr., 1993), 41(4), 363–366.
K. Allenby et al., *Angiology*, (1991), 42, 418–420.
H. Hamilton et al., *J. Med. Chem.*, (1987), 30, 91–96.
H. Padma–Nathan et al., *Sem. in Urol.*, (Nov., 1986), vol. IV, No. 4, 236–238.
J. Beavo et al., *TiPS*, (Apr., 1990), 11, 150–155.
S. Korenman et al., *Clin. Res.*, (1988), 36, 123A.
D. Halsted et al., *J. Urol.*, (Jul., 1986), 136, 109–110.
W. Thompson, *Pharmac. Ther.*, (1991), 51, 13–33.
M. Giembycz et al., *Clin. and Exper. Allergy*, (1992), 22, 337–344.
C. Nicholson et al., *Tips*, (Jan., 1991), 12, 19–27.
J. LeBlanc et al., *Eur. J. Cardiothorac Surg.*, (1993), 7, 211–215.
C. Stief et al., *J. Urol.*, (Nov., 1992), 148, 1437–1440.
C. Stief et al., *World J. Urol.*, (1991), 9, 237–239.
C. Clyne et al., *Br. J. Surg.*(Apr., 1987), 74, 246–248.
V. Mirone et al., *Acta. Urol. Ltd.*, (1992), Suppl. 4, 11–12.
P. Bush, Ph.D. Thesis (1992), pp. 159–160.
T. Lincoln, *Pharmac. Ther.*, (1989), 41, 479–502.
J. Heaton et al., *Urology*, (Feb., 1995), 45(2), 200–206.
Beyer et al., *Phys. and Behav.*, (1981), 27, 731–733.
Pickard et al., *Br. J. Pharmacol.*, (1991), 104 755–759.
Martinez–Pineiro et al., *Eur. Urol.*, (1993), 24, 492–499.
Mirone et al., *Br. J. Pharmacol.*, (Mar., 1993), 71(3), 365.
Murray et al., *Biochemical Soc. Trans.*, (1992), 20, 460–464.
Raeburn et al., *Prog. Drug Res.*, (1993), 12–32.
Merkel, *Cardio. Drug. Rev.*, (1993), 11(4), 501–515.
"Physicians' desk Reference," (1992) 2207–2208.
Cimino et al. *Biochem. Pharmacology*, (1988), 37(14), 2739–2745.
Watanabe et al., *Federation Proceedings*, (1982), 41(7), 2292–2399.
Earl et al., *Life Sciences*, (1984), 35, 525–534.
Brindley, *Brit. J. Phychiat.*, (1983), 143, 332–337.
Keogh, *Aust. NZ. J. Med.*, (1989), 19, 108–112.
Funderbunk, *New Engl. J. Med.*, (1974), 290, 630–631.
Beretta, *Acta European Fertilitatis*(1986), 17, 43–45.
"Physicians' Desk Reference," (1992), 1778–1779.

\* cited by examiner

USE OF CGMP PHOSPHODIESTERASE INHIBITORS IN METHODS TO TREAT FEMALE SEXUAL DYSFUNCTION

CROSS-REFERENCE TO RELATED APPLICATION

This application is a continuation of application Ser. No. 08/981,989, filed Sep. 10, 1998, now U.S. Pat. No. 6,140,329, which is based on PCT/EP96/03024, filed Jul. 11, 1996.

This invention relates to the use of tetracyclic derivatives which are potent and selective inhibitors of cyclic guanosine 3',5'-monophosphate specific phosphodiesterase (cGMP specific PDE) in the treatment of impotence.

Impotence can be defined as a lack of power, in the male, to copulate and may involve an inability to achieve penile erection or ejaculation, or both. More specifically, erectile impotence or dysfunction may be defined as an inability to obtain or sustain an erection adequate for intercourse. Its prevalence is claimed to be between 2 and 7% of the human male population, increasing with age, up to 50 years, and between 18 and 75% between 55 and 80 years of age.

Reports of well-controlled clinical trials in man are few and the efficacy of orally administered drugs is low. Although many different drugs have been shown to induce penile erection, they are only effective after direct injection into the penis, e.g. intraurethrally or intracavemosally (i.c.), and are not approved for erectile dysfunction. Current medical treatment is based on the i.c. injection of vasoactive substances and good results have been claimed with phenoxybenzamine, phentolamine, papaverine and prostaglandin $E_1$, either alone or in combination; however, pain, priapism and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

As a general alternative to pharmacological intervention, a variety of penile prostheses has been used to assist achievement of an erection. The short term success rate is good, but problems with infection and ischaemia, especially in diabetic men, make this type of treatment a final option rather than first-line therapy.

The compounds of the invention are potent inhibitors of cyclic guanosine 3',5'-monophosphate phosphodiesterases (cGMP PDEs). GB 9514464.8, which is the priority document for the present application describes the syntheses of the compounds of the invention and their utility in impotence. WO95/19978, which was unpublished at the priority date of the present application, also describes the syntheses of the compounds of the invention and their utility in other diseases associated with inhibition of cGMP PDEs. The compounds may be represented by the following general formula (I):

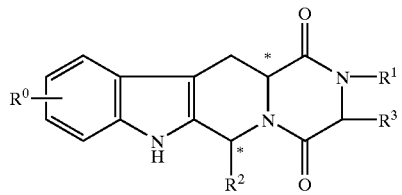

and salts and solvates (e.g. hydrates) thereof, in which:

$R^0$ represents hydrogen, halogen or $C_{1-6}$ alkyl;

$R^1$ represents hydrogen, $C_{1-6}$alkyl, $C_{2-6}$ alkenyl, $C_{2-6}$ alkynyl, halo$C_{1-6}$alkyl, $C_{3-8}$cycloalkyl, $C_{3-8}$cycloalkyl$C_{1-3}$alkyl, aryl$C_{1-3}$alkyl or heteroaryl$C_{1-3}$alkyl;

$R^2$ represents an optionally substituted monocyclic aromatic ring selected from benzene, thiophene, furan and pyridine or an optionally substituted bicyclic

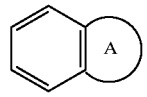

attached to the rest of the molecule via one of the benzene carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$ alkyl, or $R^1$ and $R^3$ together represent a 3- or 4- membered alkyl or alkenyl chain. Suitable individual compounds of the invention for use in the treatment of erectile dysfunction include:

Cis-2,3,6,7,12,12a-hexahydro-2-(4-pyridylmethyl)-6-(3,4-methylenedioxyphenyl)-pyrazino[2', 1':6,1]pyrido[3,4-b]indole-1,4-dione;

Cis-2,3,6,7,12,12a-hexahydro-6-(2,3-dihydrobenzo[b]furan-5-yl)-2-methyl-pyrazino[2', 1':6,1]pyrido[3,4-b]indole -1,4-dione;

Cis-2,3,6,7,12,12a-hexahydro-6-(5-bromo2-thienyl)-2-methyl-pyrazino[2', 1':6,1 ]pyrido[3,4-b]indole -1,4-dione;

Cis-2,3,6,7,12,12a-hexahydro-2-butyl-6-(4-methylphenyl)-pyrazino[2', 1':6,1 ]pyrido[3,4-b]indole-1,4-dione;

(6R,12aR)-2,3,6,7,12,12a-Hexahydro-2-isopropyl-6-(3,4-methylenedioxyphenyl)-pyrazino[2',1':6,1 ]pyrido[3,4-b]indole-1,4-dione;

(6R,12aR)-2,3,6,7,12,12a-Hexahydro-2-cyclopentyl-6-(3,4-methylenedioxyphenyl)-pyrazino[2', 1':6,1]pyrido[3,4-b]indole-1,4-dione;

(6R, 12aR)-2,3,6,7,12,12a-Hexahydro-2-cyclopropylmethyl-6-(4-methoxyphenyl)-pyrazino[2', 1':6,1]pyrido[3,4-b]indole-1,4-dione;

(6R, 12aR)-2,3,6,7,12,12a-Hexahydro-6-(3-chloro-4-methoxyphenyl)-2-methyl-pyrazino[2', 1':6,1]pyrido[3,4-b]indole-1,4-dione;

(6R,12aR)-2,3,6,7,12,12a-Hexahydro-2-methyl-6-(3,4-methylenedioxyphenyl)-pyrazino[2', 1':6,1]pyrido[3,4-b]indole-1,4-dione;

(6R, 12aR)-2,3,6,7,12,12a-Hexahydro-6-(3,4-methylenedioxyphenyl)-pyrazino[2', 1':6,1]pyrido[3,4-b]indole-1,4dione;

(5aR, 12R, 14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione;

Cis-2,3,6,7,12,12a-hexahydro-2-cyclopropyl-6-(3,4-methylenedioxyphenyl)-pyrazino[2',1':6,1]pyrido[3,4-b]indole-1,4-dione;

(3S, 6R,12aR)-2,3,6,7,12,12a-hexahydro-3-methyl-6-(3,4-methylenedioxyphenyl)-pyrazino[2', 1':6,1]pyrido[3,4-b]indole-1,4-dione;

and physiologically acceptable salts and solvates (e.g. hydrates) thereof.

The specific compounds of the invention are:

(6R, 12aR)-2,3,6,7,12,12a-hexahydro-2-methyl6-(3,4methylenedioxyphenyl)-pyrazino[2', 1':6,1]pyrido[3,4-b]indole-1,4-dione (Compound A); and (3S, 6R, 12aR)-2,3,6,7,12,12a-hexahydro-2,3-dimethyl-6-(3,4-methylenedioxyphenyl)-pyrazino[2', 1':6,1]pyrido[3,4-b]indole-1,4-dione (Compound B);

and physiologically acceptable salts and solvates (e.g. hydrates) thereof.

Unexpectedly, it has now been found that compounds of formula (I), and in particular compounds A and B, are useful in the treatment of erectile dysfunction. Furthermore the compounds may be administered orally, thereby obviating the disadvantages associated with i.c. administration. Thus the present invention concerns the use of compounds of formula (I), and in particular compounds A and B, or a pharmaceutically acceptable salt thereof, or a pharmaceutical composition containing either entity, for the manufacture of a medicament for the curative or prophylactic treatment of erectile dysfunction in a male animal, including man.

The pharmaceutically acceptable salts of the compounds of formula (I), and in particular compounds A and B which contain a basic centre are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of formula (I), and in particular compounds A and B can also provide pharmaceutically acceptable metal salts, in particular alkali metal salts, with bases. Examples include the sodium and potassium salts.

It has been shown that compounds of the present invention are potent and selective inhibitors of cGMP specific PDE. It has now been surprisingly found that human corpus cavemosum contains three distinct PDE enzymes. The predominant PDE has further surprisingly been found to be cGMP PDE. As a consequence of the selective PDE V inhibition exhibited by compounds of the present invention, the subject compounds can elevate cGMP levels, which in turn can mediate relaxation of the corpus cavemosum tissue and consequent penile erection.

Although the compounds of the invention are envisaged primarily for the treatment of erectile dysfunction or male sexual dysfunction, they may also be useful for the treatment of female sexual dysfunction including orgasmic dysfunction related to clitoral disturbances.

Generally, in man, oral administration of the compounds of the invention is the preferred route, being the most convenient and avoiding the disadvantages associated with i.c. administration. In circumstances where the recipient suffers from a swallowing disorder or from impairment of drug absorption after oral administration, the drug may be administered parenterally, e.g. sublingually or buccally.

For administration to man in the curative or prophylactic treatment of the disorders identified above, oral dosages of a compound of formula (I), and in particular compounds A and B will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, compounds of formula (I), and in particular compounds A and B can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agents (e.g. methylcellulose, a semi-synthetic glyceride such as witepsol or mixtures of glycerides such as a mixture of apricot kernel oil and PEG-6 esters or mixtures of PEG-8 and caprylic/capric glycerides).

For veterinary use, a compound of formula (I), and in particular compound A or B or a non-toxic salt thereof is administered as a suitably acceptable formulation in accordance with normal veterinary practice and the veterinary surgeon will determine the dosing regimen and route of administration which will be most appropriate for a particular male animal.

Thus the invention includes a pharmaceutical composition for the curative or prophylactic treatment of erectile dysfunction in a male animal, including man, comprising a compound of formula (I), and in particular compound A or B, or a pharmaceutically acceptable salt thereof, together with a pharmaceutically acceptable diluent or carrier.

There is further provided a process for the preparation of a pharmaceutical composition for the curative or prophylactic treatment of erectile dysfunction in a male animal, including man, comprising formulating a compound of formula (I), and in particular compound A or B, or a pharmaceutically acceptable salt thereof, with a pharmaceutically acceptable diluent or carrier.

The invention also provides a method of treating a male animal, including man, to cure or prevent erectile dysfunction which comprises treating said male animal with an effective amount of a compound of formula (I), and in particular compound A or B, or a pharmaceutically acceptable salt thereof, or a pharmaceutical composition containing either entity.

Moreover, the invention includes the use of a compound of formula (I), and in particular compound A or B, or a pharmaceutically acceptable salt thereof, or a pharmaceutical composition containing either entity, for the manufacture of a medicament for the curative or prophylactic treatment of erectile dysfunction in a male animal, including man.

A compound of formula (I), and in particular compound A or B, may also be used in combination with other therapeutic agents which may be useful in the treatment of erectile dysfunction substantially as hereinbefore described. The invention thus provides, in another aspect, a combination of a compound of formula (I), and in particular compound A or B together with another therapeutically active agent.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a compound of the invention will be readily appreciated by those skilled in the art.

The compounds of the invention may be prepared by any suitable method known in the art or by the following process which forms part of the present invention. The process has been previously substantially described in the priority document of the present invention GB9514464.8, and in WO95/19978. Thus, a process for preparing a compound of formula (I) comprises treating a compound of formula (II)

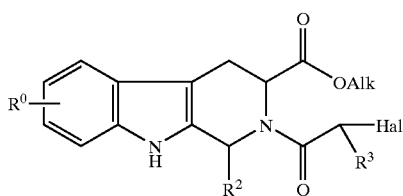

(II)

(in which Alk represents $C_{1-6}$alkyl, e.g. methyl or ethyl and Hal is a halogen atom, e.g. chlorine) with a primary amine $R^1NH_2$ in a suitable solvent such as an alcohol (e.g. methanol or ethanol) or a mixture of solvents, conveniently at a temperature of from 20° C. to reflux (e.g. at about 50° C.).

A compound of formula (II) may conveniently be prepared by treating a compound of formula (III) with a compound of formula (IV)

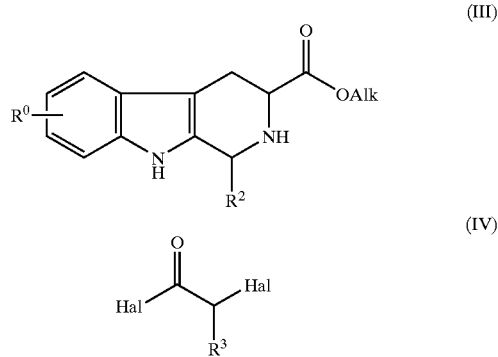

(III)

(IV)

in a suitable solvent such as a halogenated hydrocarbon (e.g. trichloromethane or dichloromethane), or an ether (e.g. tetrahydrofuran), preferably in the presence of a base such as an organic amine (e.g. a trialkylamine such as triethylamine) or an alkali metal carbonate or bicarbonate (e.g. $NaHCO_3$). The reaction may conveniently be effected at a temperature of from −20° C. to +20° C. (e.g. at about 0° C.).

A compound of formula (I) may also be prepared from a compound of formula (III) in a two-step procedure via a compound of formula (II) isolated without purification.

Compounds of formula (I) may be prepared as individual enantiomers in two steps from the appropriate enantiomer of formula (III) or as mixtures (e.g. racemates) of either pairs of cis or trans isomers from the correspondong mixtures of either pairs of cis or trans isomers of formula (III).

Individual enantiomers of the compounds of the invention may be prepared from racemates by resolution using methods known in the art for the separation of racemic mixtures into their constituent enantiomers, for example using HPLC (high performance liquid chromatography) on a chiral column such as Hypersil naphthylurea.

A compound of formula (III) may conveniently be prepared from a tryptophan alkyl ester of formula (V)

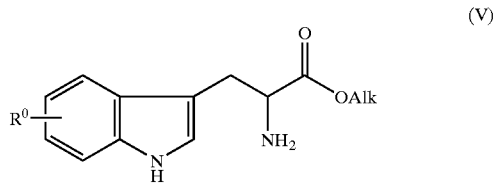

(V)

(where Alk is as previously defined) or a salt thereof (e.g. the hydrochloride salt) with an aldehyde $R^2CHO$. The reaction may conveniently be effected in a suitable solvent such as a halogenated hydrocarbon (e.g. dichloromethane) or an aromatic hydrocarbon (e.g. toluene) in the presence of an acid such as trifluoroacetic acid. The reaction may conveniently be carried out at a temperature of from −20° C. to reflux to provide a compound of formula (III) in one step. The reaction may also be carried out in a solvent such as an aromatic hydrocarbon (e.g. benzene or toluene) under reflux, optionally using a Dean-Stark apparatus to trap the water produced.

The reaction provides a mixture of cis and trans isomers which may be either individual enantiomers or racemates of pairs of cis or trans isomers depending upon whether racemic or enantiomerically pure tryptophan alkyl ester was used as the starting material. Individual cis or trans enantiomers may conveniently be separated from mixtures thereof by fractional crystallisation or by chromatography (e.g. flash column chromatography) using appropriate solvents and eluents. Similarly, pairs of cis and trans isomers may be separated by chromatography (e.g. flash column chromatography) using appropriate eluents. An optically pure trans isomer may also be converted to an optically pure cis isomer using suitable epimerisation procedures. One such procedure comprises treating the trans isomer or a mixture (e.g. 1:1 mixture) of cis and trans isomers with methanolic or aqueous hydrogen chloride at a temperature of from 0° C. to the refluxing temperature of the solution. The mixture may then be subjected to chromatography (e.g. flash column chromatography) to separate the resulting diastereoisomers, or in the procedure utilising aqueous hydrogen chloride the desired cis isomer precipitates out as the hydrochloride salt which may then be isolated by filtration.

The pharmaceutically acceptable acid addition salts of a compound of formula (I), and in particular compound A or B which contain a basic centre may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound A or B with a suitable base. Both types of salt may be formed or interconverted using ion-exchange resin techniques.

Compounds of the invention may be isolated in association with solvent molecules by crystallisation from or evaporation of an appropriate solvent.

The syntheses of compounds A and B and of the intermediates for use therein are illustrated by the following examples. The examples have been previously described in the priority document of the instant invention GB9514464.8, and the corresponding Intermediate or Example numbers therein are shown in parentheses next to the current Intermediate or Example number.

In the Examples section hereinafter the following abbreviations are used:

MeOH (methanol) and EtOH (ethanol),

INTERMEDIATE 1 (54)

(1R,3R)-Methyl 1,2,3,4-Tetrahydro-1-(3,4-methylenedioxyphenyl)-9H-pyrido[3,4-b]indole-3-carboxylate, cis Isomer To a stirred solution of D-tryptophan methyl ester (11 g) and piperonal (7.9 g) in anhydrous $CH_2Cl_2$ (400 mL) cooled at 0° C. was added dropwise trifluoroacetic acid (7.7 mL) and the solution was allowed to react at ambient temperature. After 4 days, the yellow solution was diluted with $CH_2Cl_2$ (200 mL) and washed with a saturated aqueous solution of $NaHCO_3$, then with water (3×200 mL) and dried over $Na_2SO_4$. The organic layer was evaporated under reduced pressure and the residue containing the two geometric isomers was purified by flash chromatography eluting with dichloromethane/ethyl acetate (97/3) to give as the first eluting product the title compound (6.5 g).

m.p.: 154° C.

INTERMEDIATE 2 (83)

(1R, 3R)-Methyl 1,2,3,4-tetrahydro-2-2-(2-chloropropionyl)-1-(3,4-methylenedioxyphenyl)-9Hpyrido[3,4-b]indole-3-carboxylate To a solution of (R)-(+)-2-chloropropionic acid (191 µl, 2.2 mmol) in anhydrous dichloromethane (30 mL), was added dicyclohexylcarbodiimide (0.45 g, 2.2 mol). Intermediate 1 (0,7 g, 2 mmol) was then added and the mixture was stirred at room temperature for 20 hours. The formed precipitate of dicyclohexylurea was removed by filtration, the filtrate was evaporated in vacuo and the crude product was purified by flash chromatography eluting with toluene/ethyl acetate: 95/15. The oily compound obtained was then crystallised from ether/hexane to give the title compound as pale yellow crystals (0.74 g).

m.p. 126–128° C.

EXAMPLE 1 (78) (COMPOUND A)

(6R, 12aR)-2,3,6,7,12,12a-Hexahydro-2-methyl-6-(3,4-methylenedioxyphenyl)-pyrazino[2', 1':6,1] pyrido[3,4-]indole-1,4-dione a) To a stirred solution of intermediate 1 (0.5 g) and $NaHCO_3$ (0.14 g) in anhydrous $CHCl_3$ (20 mL) was added dropwise chloroacetyl chloride (0.27 mL) at 0° C. The resulting mixture was stirred for 1 hour at the same temperature and diluted with $CHCl_3$ (20 mL). Water (10 mL) was then added dropwise with stirring to the mixture, followed by a saturated solution of $NaHCO_3$. The organic layer was washed with water until neutrality and dried over $Na_2SO_4$. After evaporation of the solvent under reduced pressure, (6R,12aR)-methyl 1,2,3,4-tetrahydro-2-chloroacetyl-1-(3,4-methylenedioxyphenyl)-9H-pyrido[3,4-b]indole-3-carboxylate was obtained as an oil which was crystallised from ether to give a solid (0.38 g, m.p.:233° C.) which was used without further purification in the next step.

b) To a stirred suspension of the chloroacetyl intermediate (0.37 g) in MeOH (20 mL) was added at room temperature a solution of methylamine (33% in EtOH) (0.4 mL) and the resulting mixture was heated at 50° C. under $N_2$ for 16 hours. The solvent was removed under reduced pressure and the residue was dissolved in $CH_2Cl_2$ (50 mL). After washing with water (3×20 mL), drying over $Na_2SO_4$ and evaporating to dryness, the residue was purified by flash chromatography eluting with $CH_2Cl_2$/MeOH (99/1) and recrystallised from 2-propanol to give the title compound as white crystals (0.22 g).

m.p.:302–303° C. Analysis for $C_{22}H_{19}N_3O_4$: Calculated: C, 67.86; H, 4.92; N, 10.79; Found: C, 67.77; H, 4.92; N, 10.74%. $[\alpha]^{20°}_D$=+71.0° (C=1.00; $CHCl_3$).

EXAMPLE 2 (117) (COMPOUND B)

(3S, 6R, 12aR)-2,3,6,7,12,12a-hexahydro-2,3-dimethyl-6-(3,4-methylenedioxyphenyl)-pyrazino[2', 1':6,1]pyrido[3,4-b]indole-1,4-dione To a stirred solution of intermediate 2 (0.3 g, 0.68 mmol) in THF (30 mL) was added at room temperature a solution of methylamine (33% in EtOH) (0.68 mL) and the resulting solution was treated at reflux under $N_2$ for 6 days. The solvent was removed under reduced pressure and the residue was dissolved in $CH_2Cl_2$ (50 mL). After washing with water (2,25 mL), drying over $Na_2SO_4$ and evaporating to dryness, the crude product was purified by flash chromatography eluting with dichloromethane/methanol:99/1. The oily residue obtained was crystallised from methanol to give the title compound as white crystals (40 mg)

m.p.: 307–309° C. Analysis for $C_{23}H_{21}N_3O_4$: Calculated: C, 68.47; H, 5.25; N, 10.42; Found: C, 68.35; H, 5.33; N, 10.42%. $[\alpha]^{20°}_D$=+65.2° (c=1.15; $CHCl_3$). The following compound was similarly prepared:

EXAMPLE 3

(3S, 6R,12aR)-2,3,6,7,12,12a-Hexahydro-3-methyl-6-(3,4-methylenedioxyphenyl)-pyrazino[2', 1':6,1] pyrido[3,4-b]indole-1,4-dione as White Crystals Using Ammonia as the Base.

m.p.:319–321° C. Analysis for $C_{22}H_{19}N_3O_4$: Calculated: C, 67.86; H, 4.92; N, 10.79; Found: C, 67.86; H, 5.17; N, 10.72%. $[\alpha]^{20°}_D$=+107° (c=1; pyridine).

Compounds A and B have been included in pharmacy formulations and details of such formulations are given below.

TABLETS FOR ORAL ADMINISTRATION

A. Direct Compression

| 1. | mg/tablet |
|---|---|
| Active ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active ingredient | 50.0 |
| Colloidal Silicon Dioxide | 0.5 |

-continued

| 2. | mg/tablet |
|---|---|
| Crospovidone | 8.0 |
| Sodium Lauryl Sulphate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active ingredient | 50.0 |
| Polyvinyl pyrollidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinyl pyrollidone, polyethylene glycol and polysorbate 80 were dissolved in water. The resultant solution was used to granulate the active ingredient. After drying the granules were screened, then extruded at elevated temperatures and pressures. The extrudate was milled and/or screened then was blended with the microcrystalline cellulose, croscarmellose sodium, colloidal silicon dioxide and magnesium stearate. The resultant mix was compressed into tablets.

| 2. | mg/tablet |
|---|---|
| Active ingredient | 50.0 |
| Polysorbate 80 | 3.0 |
| Lactose Ph Eur | 178.0 |
| Starch BP | 45.0 |
| Pregelatinised Maize Starch BP | 22.5 |
| Magnesium Stearate BP | 1.5 |

The active ingredient was sieved and blended with the lactose, starch and pregelatinised maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths may be prepared by altering the ratio of active ingredient to the other excipients.

FILM COATED TABLETS

The aforementioned tablet formulations were film coated.

| Coating Suspension | % w/w |
|---|---|
| Opadry white† | 13.2 |
| Purified water Ph Eur | to 100.0* |

*The water did not appear in the final product. The maximum theoretical weight of solids applied during coating was 20 mg/tablet.
†Opadry white is a proprietary material obtainable from Colorcon Limited, UK which contains hydroxypropyl methylcellulose, titanium dioxide and triacetin.

The tablets were film coated using the coating suspension in conventional film coating equipment.

CAPSULES

| 1. | mg/capsule |
|---|---|
| Active ingredient | 50.0 |
| Lactose | 148.5 |
| Polyvinyl pyrollidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses may be prepared by altering the ratio of active ingredient to excipient, the fill weight and if necessary changing the capsule size.

| 3. | mg/capsule |
|---|---|
| Active ingredient | 50.0 |
| Labrafil M1944CS | to 1.0 ml |

The active ingredient was sieved and blended with the Labrafil. The suspension was filled into soft gelatin capsules using appropriate equipment.

What is claimed is:

1. A method for the treatment of female sexual dysfunction related to clitoral disturbances, comprising administration of a PDEV inhibitor of formula (I):

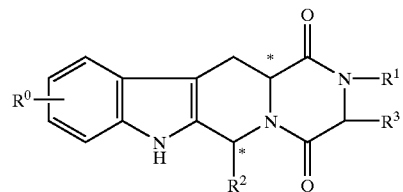

and salts and solvates (e.g., hydrates) thereof, in which:

$R^0$ represents hydrogen, halogen, or $C_{1-6}$alkyl;

$R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl $C_{1-3}$alkyl, aryl$C_{1-3}$alkyl, or heteroaryl$C_{1-3}$alkyl;

$R^2$ represents an optionally substituted monocyclic aromatic ring selected from benzene, thiophene, furan, and pyridine or an optionally substituted bicyclic ring

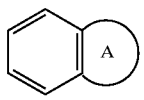

attached to the rest of the molecule via one of the benzene ring carbon atoms and wherein the fused ring A is a 5- or 6-membered ring which can be saturated or partially or fully unsaturated and comprises carbon atoms and optionally one or two heteroatoms selected from oxygen, sulphur, and nitrogen; and $R^3$ represents hydrogen or $C_{1-3}$alkyl, or $R^1$ and $R^3$ together represent a 3- or 4-membered alkyl or alkenyl chain.

2. The method of claim 1 wherein the compound of formula (I) is administered orally.

3. The method of claim 1 wherein the sexual dysfunction is an orgasmic dysfunction.

4. A method for the treatment of female sexual dysfunction related to clitoral disturbances, comprising administration of a PDEV inhibitor selected from the group consisting of cis-2,3,6,7,12,12a-hexahydro-2-(4-pyridylmethyl)-6-(3,4-methylenedioxyphenyl)pyrazino[2', 1':6,1]pyrido[3,4-b]-indole-1,4-dione;

cis-2,3,6,7,12,12a-hexahydro-6-(2,3-dihydrobenzo[b]furan-5-yl)-2-methylpyrazino[2', 1':6,1]pyrido[3,4-b]indole-1,4-dione;

cis-2,3,6,7,12,12a-hexahydro-6-(5-bromo-2-thienyl)-2-methylpyrazino[2', 1':6,1]pyrido[3,4-b]indole-1,4-dione;

cis-2,3,6,7,12,12a-hexahydro-2-butyl-6-(4-methylphenyl)-pyrazino[2', 1':6,1]pyrido[3,4-b]indole-1,4-dione;

(6R,12aR)-2,3,6,7,12,12a-hexahydro-2-isopropyl-6-(3,4-methylenedioxyphenyl)pyrazino[2', 1':6,1]pyrido[3,4-b]-indole-1,4-dione;

(6R,12aR)-2,3,6,7,12,12a-hexahydro-2-cyclopentyl-6-(3,4-methylenedioxyphenyl)pyrazino[2', 1':6,1]pyrido[3,4-b]-indole-1,4-dione;

(6R,12aR)-2,3,6,7,12,12a-hexahydro-2-cyclopropylmethyl-6-(4-methoxyphenyl)pyrazino[2', 1'1:6,1]pyrido[3,4-b]indole-1,4-dione;

(6R,12aR)-2,3,6,7,12,12a-hexahydro-6-(3-chloro-4-methoxyphenyl)-2-methylpyrazino[2', 1':6,1]pyrido[3,4-b]indole-1,4-dione;

(6R,12aR)-2,3,6,7,12,12a-hexahydro-2-methyl-6-(3,4-methylenedioxyphenyl)pyrazino[2', 1':6,1]pyrido[3,4-b]-indole-1,4-dione;

(6R,12aR)-2,3,6,7,12,12a-hexahydro-6-(2,4-methylenedioxyphenyl)pyrazino[2', 1':6,1]pyrido[3,4-b]indole-1,4-dione;

(5a,12R,14aS)-1,2,3,5,6,11,12,14a-octahydro-12-(3,4-methylenedioxyphenyl)pyrrolo[1",2":4',5']pyrazino-[2', 1':6,1]pyrido[3,4-b]indole-5-1,4-dione;

cis-2,3,6,7,12,12a-hexahydro-2-cyclopropyl-6-(3,4-methylenedioxyphenyl)pyrazino[2', 1':6,1]pyrido[3,4-b]indole-1,4-dione;

(3S,6R,12aR)-2,3,6,7,12,12a-hexahydro-3-methyl-6-(3,4-methylenedioxyphenyl)pyrazino[2', 1':6,1]pyrido[3,4-b]-indole-1,4-dione;

and physiologically acceptable salts and solvates thereof.

5. A method of claim 4 wherein the compound is administered orally.

6. A method for the treatment of female/sexual dysfunction related to clitoral disturbances, comprising administration of a PDEV inhibitor selected from the group consisting of (6R,12aR)-2,3,6,7,12,12a-hexahydro-2-methyl-6-(3,4-methylenedioxyphenyl)pyrazino[2', 1':6,1]pyrido[3,4-b]-indole-1,4-dione;

(3S,6R,12aR)-2,3,6,7,12,12a-hexahydro-2,3-dimethyl-6-(3,4-methylenedioxyphenyl)pyrazino[2', 1':6,1]pyrido[3,4-b]indole-1,4-dione;

and physiologically acceptable salts and solvates thereof.

7. The method of claim 6 wherein the compound is administered orally.

8. A method of treating a female animal for sexual dysfunction related to clitoral disturbances which comprises treating said female animal with an effective amount of a pharmaceutical composition comprising a PDEV inhibitor selected from the group consisting of cis-2,3,6,7,12,12a-hexahydro-2-(4-pyridylmethyl)-6-(3,4-methylenedioxyphenyl)pyrazino[2', 1':6,1]pyrido[3,4-b]-indole-1,4-dione;

cis-2,3,6,7,12,12a-hexahydro-6-(2,3-dihydrobenzo[b]furan-5-yl)-2-methylpyrazino[2', 1':6,1]pyrido[3,4-b]indole-1,4-dione;

cis-2,3,6,7,12,12a-hexahydro-6-(5-bromo-2-thienyl)-2-methylpyrazino[2',1':6,1]pyrido[3,4-b]indole-1,4-dione;

cis-2,3,6,7,12,12a-hexahydro-2-butyl-6-(4-methylphenyl)-pyrazino[2', 1':6,1]pyrido[3,4-b]indole-1,4-dione;

(6R,12aR)-2,3,6,7,12,12a-hexahydro-2-isopropyl-6-(3,4-methylenedioxyphenyl)pyrazino[2',1':6,1]pyrido[3,4-b]-indole-1,4-dione;

(6R,12aR)-2,3,6,7,12,12a-hexahydro-2-cyclopentyl-6-(3,4-methylenedioxyphenyl)pyrazino[2', 1':6,1]pyrido[3,4-b]-indole-1,4-dione;

(6R,12aR)-2,3,6,7,12,12a-hexahydro-2-cyclopropylmethyl-6-(4-methoxyphenyl)pyrazino[2', 1':6,1]pyrido[3,4-b]indole-1,4-dione;

(6R,12aR)-2,3,6,7,12,12a-hexahydro-6-(3-chloro-4-methoxyphenyl)-2-methylpyrazino[2',1':6,1]pyrido[3,4-b]indole-1,4-dione;

(6R,12aR)-2,3,6,7,12,12a-hexahydro-2-methyl-6-(3,4-methylenedioxyphenyl)pyrazino[2', 1':6,1]pyrido[3,4-b]-indole-1,4-dione;

(6R,12aR)-2,3,6,7,12,12a-hexahydro-6-(3,4-methylenedioxyphenyl)pyrazino[2',1':6,1]pyrido[3,4-b]indole-1,4-dione;

(5aR,12R,14aS)-1,2,3,5,6,11,12,14a-octahydro-12-(3,4-methylenedioxyphenyl)pyrrolo[1",2":4',5']pyrazino-[2', 1':6,1]pyrido[3,4-b]indole-5-1,4-dione;

cis-2,3,6,7,12,12a-hexahydro-2-cyclopropyl-6-(3,4-methylenedioxyphenyl)pyrazino[2',11:6,1]pyrido[3,4-b]-indole-1,4-dione;

(3S,6R,12aR)-2,3,6,7,12,12a-hexahydro-3-methyl-6-(3,4-methylenedioxyphenyl)pyrazino[2',1':6,1]pyrido[3,4-b]-indole-1,4-dione;

and physiologically acceptable salts and solvates thereof, together with a pharmaceutically acceptable diluent or carrier.

* * * * *

UNITED STATES PATENT AND TRADEMARK OFFICE
CERTIFICATE OF CORRECTION

PATENT NO.    : 6,608,065 B1
DATED         : August 19, 2003
INVENTOR(S)   : Daugan It is certified that error appears in the above-identified patent and that said Letters Patent is hereby corrected as shown below:

Title page, Item [54] and Column 1, line 1,
Title, "CGMP PHOSPHODIESTERASE" should be
-- cGMP PHOSPHODIESTERASE --
Item [56], References Cited, OTHER PUBLICATIONS, "Read" reference, "Intermational" should be -- International --; "Brindley" reference, "19, 108-112" should be -- 143, 332-337 --; Delete duplicated references starting with "Beyer et al." and continuing through "Brindley" and then starting with "Funderbunk" continuing through "Physician's Desk" reference.
Item [57], ABSTRACT,
Line 4, "methylenedioxyphenyl)pyrazino" should be -- methylenedioxyphenyl)-pyrazino --

Column 1,
Line 33, "intracavemosally" should be -- intracavernosally --

Column 2,
Line 20, "bicyclic" should be -- bicyclic ring --
Line 28, "benzene carbon atoms" should be -- benzene ring carbon atoms --
Line 43, "bromo2" should be -- bromo-2 --

Column 3,
Lines 13-14, "methyl6-" should be -- methyl-6- --
Lines 47 and 52, "cavemosum" should be --cavernosum --
Line 32, "-2-2-(2-chloropropionyl)" should be -- -2-(2-chloropropionyl) --

Column 7,
Line 34, "9Hpyrido" should be -- 9H-pyrido --
Line 43, "95/15." should be -- 95/5. --
Line 52, "[3,4-]" should be -- [3,4-b] --

Column 8,
Line 25, "(2,25mL)," should be -- (2.25mL), --

Column 10,
Line 63, "$C_{3-8}$cycloalkyl $C_{1-3}$alkyl" should be -- $C_{3-8}$cycloalkyl$C_{1-3}$alkyl --

UNITED STATES PATENT AND TRADEMARK OFFICE
CERTIFICATE OF CORRECTION

PATENT NO. : 6,608,065 B1
DATED : August 19, 2003
INVENTOR(S) : Daugan

It is certified that error appears in the above-identified patent and that said Letters Patent is hereby corrected as shown below:

Column 11,
Line 26, "[3,4-b]-indole-1" should be -- [3,4-b]indole-1 --
Line 35, "methylphenyl)-pyrazino" should be -- methylphenyl)pyrazino --
Lines 39, 41-42, 50-51 and 64, "[3,4-b]-indole" should be -- [3,4-b]indole --
Lines 44-45, "[2',1'1:6,1]" should be -- [2',1':6,1] --
Lines 56-57, "pyrazino-[2',1':6,1]" should be -- pyrazino[2',1':6,1] --

Column 12,
Line 1, "female/sexual" should be -- female sexual --
Lines 7, 23, 35-36, 38-39, 45-46, 48-49 and 60-61, "[3,4-b]-indole" should be -- [3,4-b]indole --
Lines 31-32, "methylphenyl)-pyrazino" should be -- methylphenyl)pyrazino --
Lines 54-55, "pyrazino-[2',1':6,1]" should be -- pyrazino[2',1':6,1] --
Lines 57-58, "[2',11:6,1]pyrido[3,4-b]-indole" should be -- [2',1':6,1]pyrido[3,4-b]indole --

Signed and Sealed this

Eleventh Day of May, 2004

JON W. DUDAS
*Acting Director of the United States Patent and Trademark Office*